US00PP36795P2

(12) United States Plant Patent
Gonzalez et al.

(10) Patent No.: US PP36,795 P2
(45) Date of Patent: Jul. 1, 2025

(54) ***GRAPTOVERIA* PLANT NAMED 'STARFIRE'**

(50) Latin Name: ***Graptoveria* hybrid**
Varietal Denomination: STARFIRE

(71) Applicant: Suculentia C.B., Tomelloso (ES)

(72) Inventors: Leo Gonzalez, Tomelloso (ES); Rafa Navarro, Tomelloso (ES)

(73) Assignee: Suculentia C.B. (ES)

( * ) Notice: Subject to any disclaimer, the term of this patent is extended or adjusted under 35 U.S.C. 154(b) by 0 days.

(21) Appl. No.: 18/778,003

(22) Filed: Jul. 19, 2024

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 5/02; A01H 5/12
See application file for complete search history.

*Primary Examiner* — Kent L Bell
(74) *Attorney, Agent, or Firm* — Cassandra Bright

(57) ABSTRACT

A new and distinct *Graptoveria* cultivar named 'Starfire' is disclosed, characterized by a round basal rosette with abundant leaves. Plants grow to no more than 18 cm in diameter. The foliage is pistachio green, developing a pink blush during the summer. The apex of the foliage is uniquely serrate, with extended serrations. The petal apex is distinguished by unique serration. The new variety would typically be produced for a variety of ornamental purposes.

3 Drawing Sheets

Latin name of the genus and species: *Graptoveria* hybrid.
Variety denomination: 'STARFIRE'.

BACKGROUND OF THE INVENTION

The new cultivar, *Graptoveria* 'STARFIRE', is the product of a planned breeding program. The new variety was selected as a single plant in a seedbed of *Graptopetalum filiferum* x *Echeveria lilacina* seedling crosses. The crossing producing the seedlings in this bed was made during 2018. Selection of 'Starfire' was made during 2019. Both crossing and selection were made in a commercial nursery in Tomelloso, Spain. The seed parent is an unnamed, unpatented, proprietary *Graptopetalum filiferum*. The pollen parent is an unnamed, unpatented, proprietary *Echeveria lilacina*.

Asexual reproduction of the new cultivar 'STARFIRE' was first performed during 2019 in Tomelloso, Spain at a commercial greenhouse, by terminal vegetative cuttings. *Graptoveria* 'STARFIRE' has since produced multiple generations and has shown that the unique features of this cultivar are stable and reproduced true to type.

SUMMARY OF THE INVENTION

The cultivar 'STARFIRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'STARFIRE'. These characteristics in combination distinguish 'STARFIRE' as a new and distinct *Graptoveria* cultivar:

1 Round basal rosette with abundant leaves and growing to no more than 18 cm in diameter.
2. Pistachio green leaves with pink blush on distal end.
3. Uniquely serrated foliage apex.

4. Inflorescences of approximately 20 cm high.
5. Unique flower form with a distinctly serrated petal apex.

PARENTAL COMPARISON

Plants of the new cultivar are similar to plants of the seed parent, in most horticultural characteristics, however, plants of the new cultivar differ in the following;

1. *Graptoveria* 'Starfire' has a unique serrate foliar apex; the seed parent has an acute and entire leaf apex.

Plants of the new cultivar are similar to plants of the pollen parent, in most horticultural characteristics, however, plants of the new cultivar differ in the following;

1. *Graptoveria* 'Starfire' has a unique serrate foliar apex; the pollen parent has an acute and entire leaf apex.
2. *Graptoveria* 'Starfire' has a unique serrate petal apex with 3 to 5 distinct teeth; the pollen parent has an acute and entire petal apex.

COMMERCIAL COMPARISON

The new cultivar 'Starfire' can be compared to the unpatented commercial variety *Graptoveria* 'Debbie'. Plants of the *Graptoveria* 'Debbie' are similar to plants of the new cultivar 'Starfire' in most horticultural characteristics. However, the new cultivar 'Starfire' differs in the following:

1. Foliage color of *Graptoveria* 'Starfire' is pistachio green, developing a blush pink; foliage color of *Graptoveria* 'Debbie' is a pruinose violet, with no rose blush.
2. *Graptoveria* 'Starfire' has a unique serrate foliar apex; 'Debbie' has an acute and entire leaf apex.
3. *Graptoveria* 'Starfire' has a unique serrate petal apex with 3 to 5 distinct teeth; 'Debbie' has an acute and entire petal apex.

The new cultivar 'Starfire' can be compared to the unpatented commercial variety *Graptoveria* 'Fred Ives'.

Plants of *Graptoveria* 'Fred Ives' are similar to plants of the new cultivar 'Starfire' in most horticultural characteristics. However, plants of the new cultivar 'Starfire' differ in the following:

1. *Graptoveria* 'Starfire' produces a tighter, denser rosette with more foliage than that of 'Fred Ives'.
2. *Graptoveria* 'Starfire' has a unique serrate foliar apex; 'Fred Ives' has an acute and entire leaf apex.
3. *Graptoveria* 'Starfire' has a unique serrate petal apex with 3 to 5 distinct teeth; 'Fred Ives' has an acute and entire petal apex.
4. *Graptoveria* 'Starfire' has flowers colored white on the upper side, light pink on the under side; 'Fred Ives' has pale yellow flowers with a bright orange center not found in the new variety.

BRIEF DESCRIPTION OF THE PHOTOGRAPHS

Figure 1:
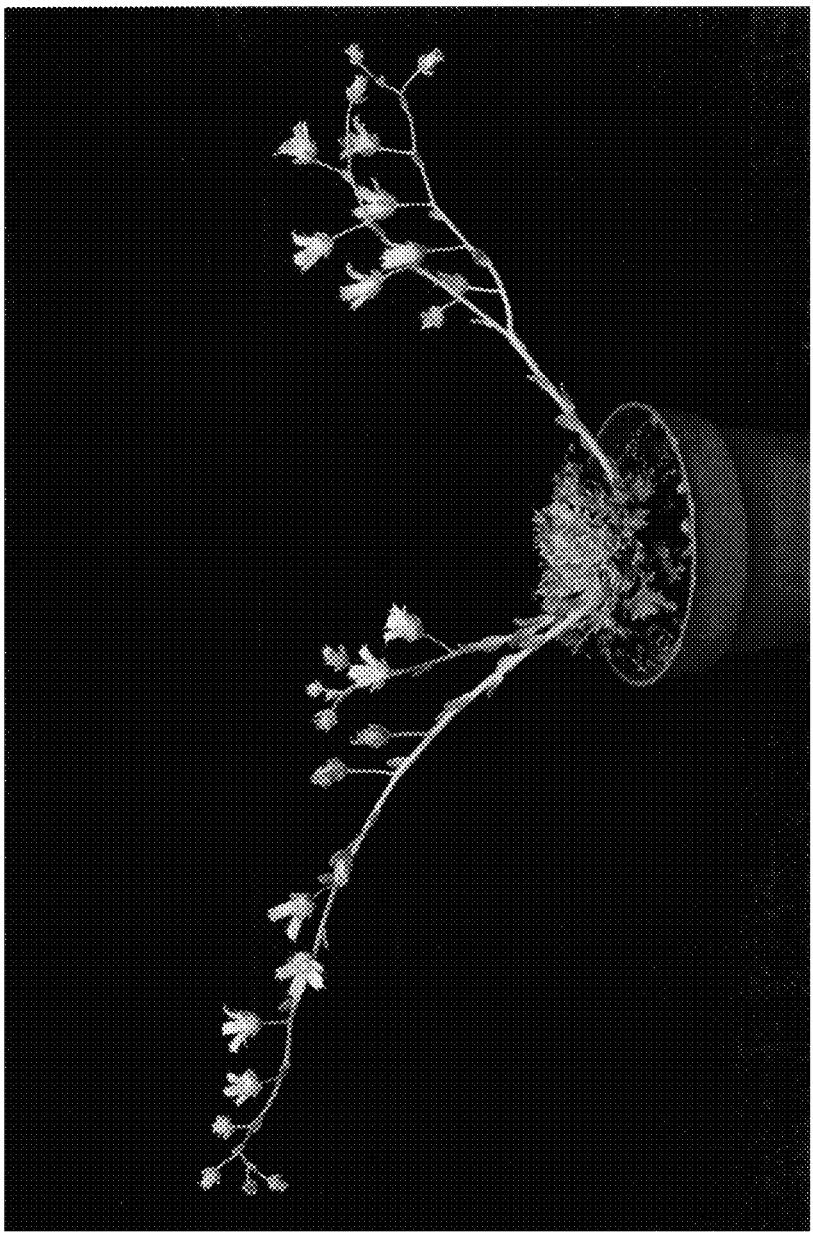
FIG. 1 illustrates in full color a typical flowering plant of 'STARFIRE' grown in a greenhouse in Ciudad Real, Spain and photographed in June. The plant is approximately 2 years old.
Figure 2:
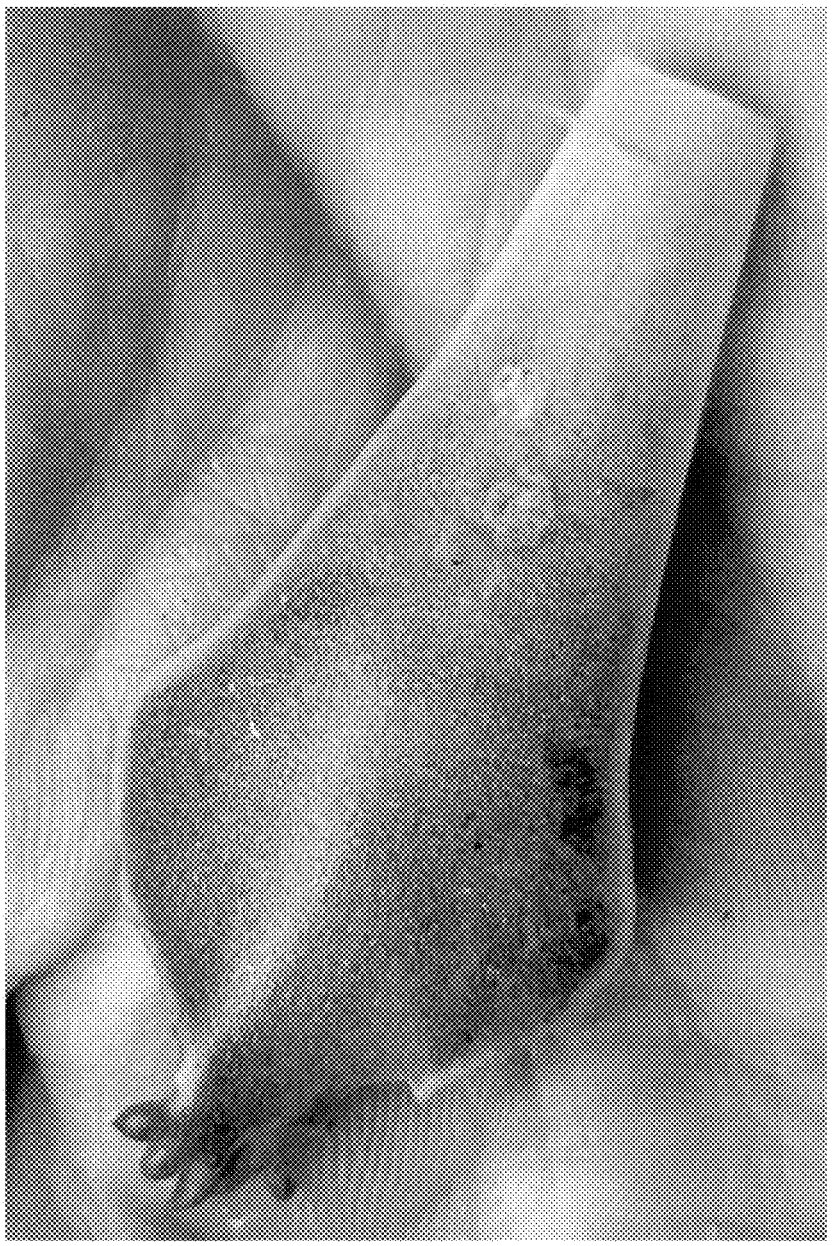
FIG. 2 is a close-up view of developing foliage in the Spring, with the apical serrations just developing.
Figure 3:
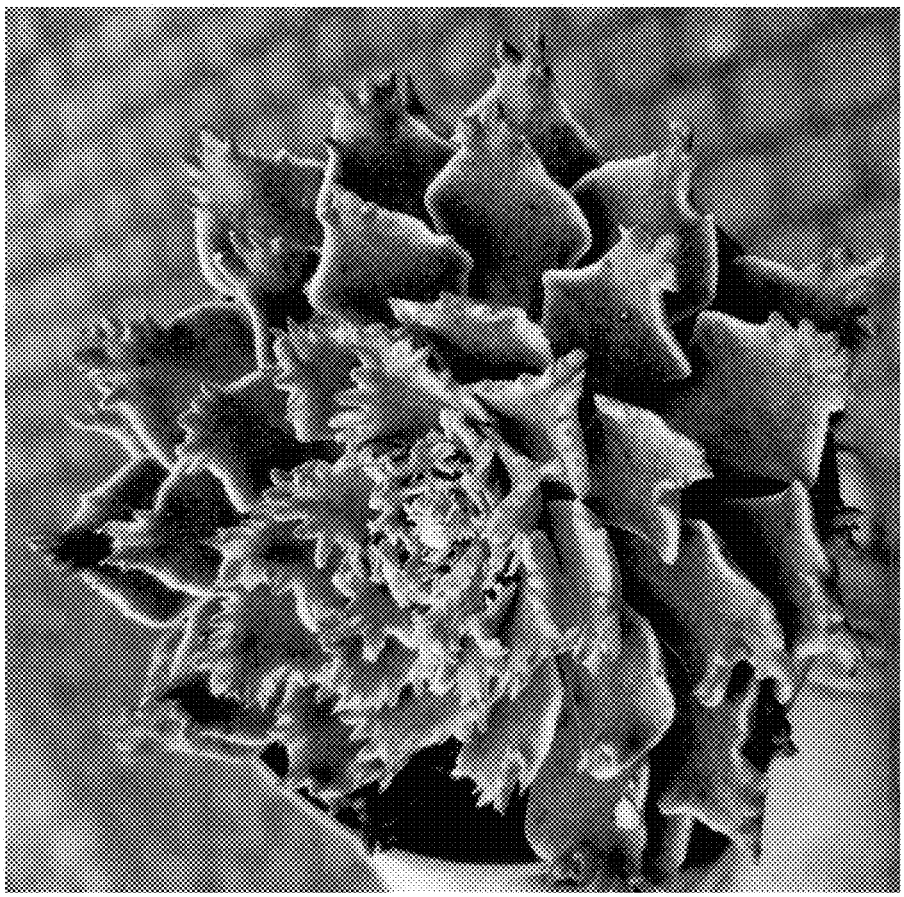
FIG. 3 is a top view of a mature 3 year old plant with fully developed apical serrations on the foliage.

The photographs were taken using conventional techniques and equipment. While the colors in this photograph may display variances of color as compared to the living cultivar, due to LRV (light reflectance value), they are as accurate as possible using conventional photographic techniques. Colors in the photograph may appear to differ slightly from the color values cited in the botanical description, which accurately describe the colors of the new *Graptoveria* plant. No artificial light, photoperiodic treatments or chemical treatments were given to the plants.

DETAILED BOTANICAL DESCRIPTION

In the following description, color references are made to The Royal Horticultural Society Colour Chart 2015 $6^{th}$ edition, except where general terms of ordinary dictionary significance are used. The following observations and measurements describe 'Starfire' plants grown outdoors in Lier, Belgium. Temperatures ranged from −1° C. to 24° C. night and day. No artificial light, photoperiodic treatments or chemical treatments were given to the plants. Measurements and numerical values represent averages of typical plant types.

Botanical classification: *Graptoveria* hybrid 'STARFIRE'.

PROPAGATION

Type of propagation typically used: Terminal vegetative cuttings.

Time to initiate roots: About 11 days at approximately 24° C.

Root description: Fibrous, creamy white to tan.

PLANT

Age of plant described: Approximately 1.5 months from a cutting.

Container size of the plant described: 9 cm.

Growth habit: Flattened rosulate plant.

Height: Approximately 3 to 5 cm to top of foliage.

Plant spread: Approximately 15 to 18 cm.

Growth rate: Slow.

Branching characteristics: Not typically observed.

FOLIAGE

Arrangement: Rosulate.

Average length: 2.0 to 3.2 cm.

Average width: 2.1 cm.

Aspect of leaf: Flat to very slightly cupped upward, apex slightly reflexed.

Leaf thickness: About 5 mm.

Shape of blade: Spatulate.

Apex: Serrated, forming 3 to 5 small appendages,

Base: Attenuate

Margin: Entire.

Texture of top surface: Glabrous.

Texture of bottom surface: Glabrous.

Appearance of top surface: Matte.

Appearance of bottom surface: Matte.

Quantity of leaves per plant: Average range 60 to 70.

Color:

*Young foliage*.—Spring, upper and lower surfaces: Greyed-Green 191B and 191C, tips Greyed-Red 170B and 179C. Summer, upper and lower surfaces: Greyed-Green 188B tips Red 50A.

*Mature foliage*.—Spring, upper and lower surfaces: Greyed-Green 191B and 191C, tips flushed Greyed-Red 170B and 179C. Summer, upper and lower surfaces: Greyed-Green 188B tips lightly flushed Red 50A.

FLOWER

Natural flowering season: June and July.

Inflorescence type: Upright raceme.

Lastingness: 8 to 10 weeks on the plant in good condition.

Quantity of inflorescences per plant: 2 to 4, most commonly 3 at a flowering plant at one time.

Quantity of flowers per inflorescence: 14 to 17.

Total Inflorescence size:

*Height*.—Approximately 10 cm.

*Width*.—Approximately 2.6 cm.

Corolla:

*Arrangement*.—Star-shaped, very open, fused only at base.

*Size*.—Length: Approximately 1.2 cm. Width: Approximately 1.3 cm at widest point.

*Rate of opening*.—About 7 to 9 days from bud to open flower.

*Lastingness of individual flowers*.—About 6 weeks.

Petals:

*Quantity*.—5.

*Length*.—Approximately 1.1 cm.

*Width*.—Approximately 4 mm.

*Margin*.—Entire.

*Shape*.—Narrow elliptic.

*Apex*.—Acute and dentate with 3 to 5 teeth.

*Base*.—Fused.

*Texture*.—Glabrous, all surfaces.

*Color*.—Outer surface: Near RHS Red 36C and 36D, flushed 38A and 38B. Inner surface: Near RHS White N155B with 38A apex. Apex fades to 38B with age.

Bud: (near opening):
*Shape*.—Conical.
*Length*.—Approximately 1.0 cm.
*Diameter*.—Approximately 7 mm.
*Color*.—Near Red 43A, flushed Red 41C and 41D.

Sepals:
*Number flower*.—5.
*Length*.—5 mm.
*Width*.—2 mm.
*Margin*.—Entire.
*Shape*.—Narrow deltate.
*Apex*.—Acute
*Base*.—Truncate
*Texture*.—Glabrous, upper and lower surfaces.
*Color*.—Outer: Near Green 136C and 136D, apex flushed near Greyed-Purple 187B. Inner: Near Green 138A and 138B, apex flushed near Greyed-Purple 187B.

Peduncle:
*Length*.—Average range 9 cm.
*Width*.—Approximately 3 mm.
*Strength*.—Moderate.
*Texture*.—Glabrous.
*Color*.—Lower section near Greyed-Purple N187C mixed with Greyed-Green 189B. Upper section near Greyed-Purple N187C with a faint layer of 187B and 187C.

Pedicels:
*Length*.—Average 5 mm.
*Width*.—Approximately 3 mm.
*Strength*.—Moderately strong.
*Texture*.—Glabrous.
*Color*.—Near RHS Orange-White 159A flushed Red 37A.

Bracts:
*Quantity*.—1 per flower.
*Length*.—5 mm.
*Width*.—3 to 4 mm.
*Margin*.—Entire.
*Shape*.—Ovate.
*Apex*.—Acute.
*Base*.—Truncate.
*Texture*.—Glabrous, upper and lower surfaces.
*Appearance*.—Matte.
*Color*.—Upper: Near Greyed-Purple N187B with flecks of 187B. Towards, base near Green 138B. Lower: Near Greyed-Purple N187B with flecks of 187B. Towards, base near Green 138B.

Fragrance: None detected.

REPRODUCTIVE ORGANS

Stamens: (Androecium).
*Number*.—12.
*Filament length*.—Approximately 8 mm.
*Filament color*.—Near White N155A.
*Anther length*.—2 mm.
*Anther color*.—Near RHS Yellow 8C.
*Anther shape*.—Linear.
*Pollen*.—Scant. Colored near 8D.

Pistil: (Gynoecium).
*Number*.—5.
*Length*.—Approximately 4 mm.
*Style color*.—Near White N155A.
*Stigma*.—Shape: Linear. Color: Near RHS Red 38B. Ovary Color: Near RHS Yellow-Green 145A.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: Neither resistance nor susceptibility to typical diseases and pests of *Graptoveria* has been observed.

What is claimed is:

1. A new and distinct cultivar of *Graptoveria* plant named 'STARFIRE' as herein illustrated and described.

* * * * *